United States Patent [19]

Kurozumi et al.

[11] 4,139,717
[45] Feb. 13, 1979

[54] 1,3-DICARBONYL COMPOUNDS

[75] Inventors: Seizi Kurozumi; Takeshi Toru; Toshio Tanaka; Shuzi Miura; Makiko Kobayashi, all of Hino; Sachio Ishimoto, Tokyo, all of Japan

[73] Assignee: Teijin Limited, Osaka, Japan

[21] Appl. No.: 756,739

[22] Filed: Jan. 4, 1977

Related U.S. Application Data

[62] Division of Ser. No. 554,097, Feb. 28, 1975, Pat. No. 4,009,196.

[30] Foreign Application Priority Data

Mar. 4, 1974 [JP]  Japan ................................. 49/24133

[51] Int. Cl.² ...................... C07C 65/20; C07C 69/95
[52] U.S. Cl. .................................. 562/460; 560/51; 560/52; 560/118; 560/126; 562/459; 562/500; 562/508; 260/405
[58] Field of Search .................... 560/52, 126, 51, 118; 260/515 R, 514 K, 514 G, 405

[56] References Cited

U.S. PATENT DOCUMENTS

| 2,094,453 | 9/1937 | Jaeger | 560/62 |
| 2,466,926 | 4/1949 | Bruson et al. | 260/126 |
| 2,926,180 | 2/1960 | Linn | 260/515 R |
| 3,636,009 | 1/1972 | Fieser et al. | 260/514 K |
| 3,679,752 | 7/1972 | Archer et al. | 260/514 K |

Primary Examiner—Jane S. Myers
Attorney, Agent, or Firm—Sherman & Shalloway

[57] ABSTRACT 1,3-Dicarbonyl compounds useful as medicines, agricultural chemicals, perfumes, and their intermediates are prepared by reacting a specific $\alpha,\beta$-unsaturated carbonyl compound with a specific organic copper lithium compound in the presence of an aprotic inert organic solvent, and then reacting the reaction product with an organic carboxylic acid halide or anhydride. In particular, novel 2-acyl-3-substituted cyclopentan-1-ones and 2-acyl-3-substituted cyclohexan-1-ones having important physiological activities are provided.

2 Claims, No Drawings

1,3-DICARBONYL COMPOUNDS

This is a division of application Ser. No. 554,097, filed Feb. 28, 1975, now U.S. Pat. No. 4,009,196.

This invention relates to novel 1,3-dicarbonyl compounds and a novel process for their preparation.

More specifically, this invention relates to a process for preparing 1,3-dicarbonyl compounds which comprises reacting an $\alpha,\beta$-unsaturated carbonyl compound with an organic copper lithium compound to introduce an organic group into the $\beta$-position of the carbonyl compound, and then reacting the product with an organic carboxylic acid halide or an organic carboxylic acid anhydride to introduce an acyl group into the $\alpha$-position of the carbonyl compound; and to novel 1,3-dicarbonyl compounds obtained by this process.

It is an object of this invention to provide novel 1,3-dicarbonyl compounds useful as medicines, agricultural chemicals, perfumes and intermediates of these, and a novel process for preparing these compounds.

Another object of this invention is to provide a novel process for preparing 1,3-dicarbonyl compounds in high yields from $\alpha,\beta$-unsaturated carbonyl compounds.

Still another object of this invention is to provide novel 2-acyl-3-substituted-cyclopentan- or -cyclohexan-1-ones useful as medicines, agricultural chemicals, perfumes, and their intermediates, and a process for their preparation.

Other objects and advantages of this invention will become apparent from the following description.

According to this invention, there is provided a process for preparing 1,3-dicarbonyl compounds of the following formula

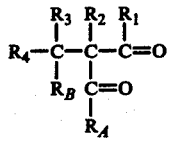
(IV)

wherein $R_1$, $R_2$, $R_3$ and $R_4$ are identical or different, and represent a hydrogen atom or a monovalent organic group, and when they are monovalent organic groups, they may be linked to each other to form rings; $R_A$ is a monovalent organic group; and $R_B$ is a monovalent organic group containing at least 2 carbon atoms, which comprises (1) reacting an $\alpha,\beta$-unsaturated carbonyl compound of the following formula

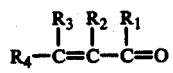
(I)

wherein $R_1$, $R_2$, $R_3$ and $R_4$ are the same as defined in formula (IV), with an organic copper lithium compound of the following formula

(II)

wherein $R_B$ is a monovalent organic group; Y is a monovalent anion; n is 1 or 2, and when n is 2, the two $R_B$ groups are identical or different, with the proviso that $R_B$ in the case of n being 1 and at least one of $R_B$ groups in the case of n being 2 are monovalent organic groups containing at least 2 carbon atoms, in the presence of an aprotic inert organic solvent, and then (2) reacting the reaction product with an acid halide or acid anhydride derived from an organic carboxylic acid of the following formula $$R_A-COCH \qquad (III)$$

wherein $R_A$ is a monovalent organic group.

Thus, the process of this invention is characterized in that substituents are successively introduced into the $\beta$-position and the $\alpha$-position of the $\alpha,\beta$-unsaturated carbonyl compound, and in particular, an acyl group is introduced into the $\alpha$-position.

Methods comprising introducing a methyl group into the $\beta$-position of an $\alpha,\beta$-unsaturated carbonyl compound, and then acetylating the resulting product have previously been known, and the following literature references report that in such methods, O-acetylation of the carbonyl compound occurs dominantly (1) E. Piers et al., "Journal of the American Chemical Society", 93, 5113 (1971).

(2) P. I. Stotter et al., "Journal of Organic Chemistry" 38, 2576 (1973).

(3) R. K. Boeckman, Jr., "Journal of Organic Chemistry", 38, 4450 (1973).

The reference (1) reports that enol acetate of the following formula

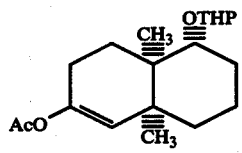
(2)

(Ac denotes $CH_3CO-$, and THP denotes a tetrahydropyranyl group)

was obtained in a yield of 88% by reacting an $\alpha,\beta$-unsaturated ketone of the following formula

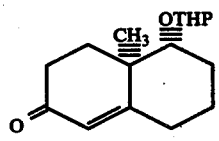
(1)

with lithium dimethylcuprate, and reacting the resulting product with acetyl chloride.

The reference (2) reports that by reacting an $\alpha,\beta$-unsaturated ketone of the following formula

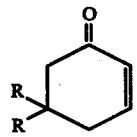
(3)

(two R groups both represent hydrogen atoms or methyl groups)

with lithium dimethylcuprate ($LiMe_2Cu$), and reacting the resulting product with an excess of acetic anhydride ($Ac_2O$), a compound of the following formula

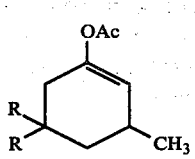

(R is the same as defined in formula (3), and Ac represents CH₃CO—)
was obtained in a yield of 90% (R=H), and 92% (R=—CH₃).

The reference (3) contains almost the same disclosure as the reference (1).

Furthermore, James A. Marshall et al., "Journal of the American Chemical Society", 91, 648 (1969) [reference (4)] discloses that enol acetate of the following formula

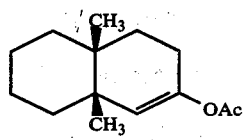

(6)

$Ac=CH_3CO—$ was obtained in a yield of 30% by reacting an $\alpha,\beta$-unsaturated ketone of the following formula

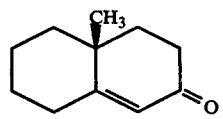

(5)

with methylmagnesium iodide, a Grignard reagent, in the presence of a copper salt, and then reacting the resulting product with acetyl chloride.

As far as the applicants are aware, there has been no other report than those in the above-cited literature references (1) to (4) regarding the alkylation and acylation of $\alpha,\beta$-unsaturated carbonyl compounds. These references commonly disclose that by methylating the $\beta$-position of the above carbonyl compound and then acetylating the product, O-acetylation of the carbonyl compound occurs dominantly.

Our investigations however led to the discovery that when an $\alpha,\beta$-unsaturated carbonyl compound such as cyclohex-2-en-1-one is reacted with an organic copper lithium compound to introduce an organic group containing at least 2 carbon atoms into the $\beta$-position of the unsaturated carbonyl compound, subsequent acylation of the resulting product unexpectedly results in the predominant C-acylation of its $\alpha$-position.

For example, according to our investigations, 2-acetyl-3-ethyl cyclohexan-1-one of the following formula

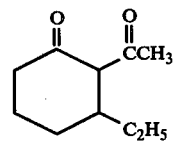

(IV-1)

was obtained in a yield of 72% by reacting cyclohex-2-en-1-one of the following formula

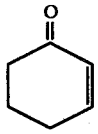

(I-1)

with lithium diethylcuprate to introduce an ethyl group into its $\beta$-position, and reacting the resulting reacting mixture with acetyl chloride, as shown hereinbelow in Example 3.

The invention will be described in greater detail below.

In the present invention, the $\alpha,\beta$-unsaturated carbonyl compound of formula (I) is first reacted with the organic copper lithium compound of formula (II) (first step). This first step will be described in detail.

FIRST STEP

I-1. $\alpha,\beta$-Unsaturated Carbonyl Compounds (I)

In the above formula (I), $R_1$, $R_2$, $R_3$ and $R_4$ are identical or different and represent a hydrogen atom or a monovalent organic group, and the organic groups may be linked to each other to form rings.

Examples of the monovalent organic group are saturated hydrocarbon groups and unsaturated hydrocarbon groups which may contain a substituent not reactive with the organic copper lithium compounds, such as alkoxy, aryloxy, siloxy, carboxy, acyloxy or carbonyl (keto, formyl). Preferred monovalent organic groups are those containing 1 to 30 carbon atoms, and the rings formed by the organic groups are preferably 5- to 7-membered.

Typical examples of the $\alpha,\beta$-unsaturated carbonyl compound of formula (I) are given below.

I-1-A. Compounds wherein $R_1$ and $R_3$ (or $R_4$) are linked to form a ring:

(a) 6-Membered Compounds

Cyclohex-2-en-1-one,
2-methylcyclohex-2-en-1-one,
3-methylcyclohex-2-en-1-one,
isophorone,
carvone,
2,3-dimethylcyclohex-2-en-1-one,
2-oxo-1-methyl-$\Delta^3$-octalin,
1-oxo-$\Delta^2$-octalin,
4-estren-3,17-dione,
1(5$\alpha$)-androsten-3,17-dione, and
5-pregnen-3$\beta$-ol-7,20-dione acetate.

(b) 5-Membered Compounds

Cyclopent-2-en-1-one,
3,4-dimethylcyclopent-2-en-1-one,
3,4,4-trimethylcyclopent-2-en-1-one,
2-methylcyclopent-2-en-1-one,
3-methylcyclopent-2-en-1-one,
4-methylcyclopent-2-en-1-one,
3-isopropylcyclopent-2-en-1-one,
2,3,4-trimethylcyclopent-2-en-1-one,
4-isopropyl-2,3-dimethylcyclopent-2-en-1-one,
3-ethyl-2-methylcyclopent-2-en-1-one,
2,3-dimethylcyclopent-2-en-1-one,
3-methyl-2-amylcyclopent-2-en-1-one,
1(8)-hydroinden-2-one,
8(9)-hydroinden-1-one, 2-hydroinden-1-one, and
4-t-butyldimethylsiloxycyclopent-2-en-1-one.

(c) 7-Membered Compounds

Cyclohept-2-en-1-one,
2-methylcyclohept-2-en-1-one, and
3,7-dimethylcyclohept-2-en-1-one.

I-1-B. Compounds wherein $R_1$ and $R_2$ are linked to form a ring:

2-Methylenecyclopentan-1-one,
2-methylenecyclohexan-1-one, and
2-propylidenecycloheptan-1-one.

I-1-C. Compounds wherein $R_2$ and $R_3$ (or $R_4$) are linked to form a ring:

1-Acetylcyclopentene,
1-cyclopentene aldehyde,
1-acetylcyclohexene,
1-cyclohexene aldehyde, and
1-acetylcycloheptene.

I-1-D. Linear compounds wherein $R_1$, $R_2$, $R_3$ and $R_4$ are not linked to each other:

Methyl vinyl ketone,
ethyl vinyl ketone,
n-propyl vinyl ketone,
n-butyl vinyl ketone,
isobutyl vinyl ketone,
n-amyl vinyl ketone,
methyl isopropenyl ketone,
ethyl isopropenyl ketone,
2-ethyl-1-hexen-3-one,
3-penten-2-one,
3-hexen-2-one,
3-hepten-2-one,
4-hexen-3-one,
7-methyl-5-octen-4-one,
5,5-dimethyl-3-hexen-2-one,
4-methyl-3-penten-2-one,
5-methyl-4-hexen-3-one,
5-ethyl-4-hepten-3-one,
3-methyl-3-hepten-2-one,
3-methyl-3-hepten-2-one,
3-n-propyl-3-hexen-2-one,
3,4-dimethyl-3-penten-2-one,
4,5-dimethyl-4-penten-3-one,
2,4,5-trimethyl-4-hexen-3-one,
acrolein,
crotonaldehyde,
methacrolein,
2-methyl-2-butenal, and
2,3-dimethyl-2-butenal.

I-2. Organic copper lithium compounds (II)

According to the process of this invention, the $\alpha,\beta$-unsaturated carbonyl compound (I) is reacted with the organic copper lithium compound of the formula $Cu(R_B)_nLiY_{2-n}$ (II) wherein the symbols are the same as defined above and when n is 2, the above formula will become $Cu(R_B)_2 \cdot Li$ (II'), in the presence of an aprotic inert organic solvent. It is presumed that as a result of this, the following reactions of formula (L) or (M), for example, take place.

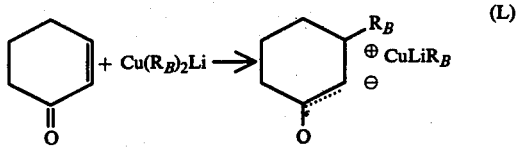

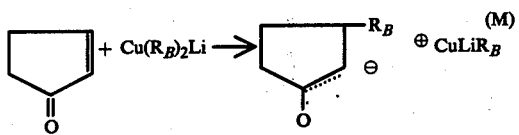

$R_B$ in formula (II) above is suitably a saturated or unsaturated hydrocarbon residue which may contain an ether linkage. Especially preferred $R_B$ groups are monovalent saturated or unsaturated hydrocarbon residues containing 2 to 20 carbon atoms which may contain an ether linkage.

Examples of $R_B$ in formula (II) are alkyl, alkenyl, aralkyl, aralkenyl, aralkynyl, alkoxyalkyl, alkoxyalkenyl, and alkoxyalkynyl groups. Preferred $R_B$ groups are monovalent organic residues containing 2 to 20 carbon atoms. Examples of Y are chlorine, bromine, iodine, and cyano group.

The organic copper lithium compound can be easily prepared by reacting a corresponding organic lithium compound with a cuprous salt in an inert medium in an atmosphere of nitrogen. At this time, the organic lithium compound is not limited to one species, but two different organic lithium compounds may be reacted with the cuprous salt stepwise or simultaneously to form an organic copper lithium compound having two different $R_B$ groups.

Examples of suitable organic lithium compounds are shown below.

Alkyllithiums (2-1) Ethyllithium
(2-2) n-Propyllithium
(2-3) i-Propyllithium
(2-4) n-Butyllithium
(2-5) t-Butyllithium
(2-6) n-Pentyllithium
(2-7) n-Hexyllithium
(2-8) Cyclohexyllithium
(2-9) n-Heptyllithium
(2-10) n-Octyllithium
(2-11) n-Nonyllithium Alkenyllithiums (2-12) Vinyllithium
(2-13) 1-Lithio-prop-cis-1-ene
(2-14) 1-Lithio-prop-trans-1-ene
(2-15) 1-Lithio-oct-cis-5-ene
(2-16) 1-Lithio-oct-trans-1-ene
(2-17) 1-Lithio-oct-cis-1-ene
(2-18) 1-Lithio-oct-trans-1-cis-5-diene Alkynyllithiums (2-19) 1-Lithio-oct-5-yne
(2-20) 1-Lithio-but-1-yne
(2-21) 1-Lithio-pent-1-yne
(2-22) 1-Lithio-hex-1-yne
(2-23) 1-Lithio-hep-1-yne
(2-24) 1-Lithio-oct-1-yne

Aralkyllithiums (2-25) 1-Lithio-8-phenyl-octene

Aralkenyllithiums (2-26) 1-(2-Thenyl)-vinyllithium
(2-27) 1-Lithio-8-phenyl-oct-trans-1-ene
(2-28) 1-Lithio-8-phenyl-oct-cis-1-ene

Aralkynyllithiums (2-29) 1-Lithio-8-phenyl-oct-5-yne

Alkoxyaralkyllithiums (2-30) 1-Lithio-3-tetrahydropyranyloxy-octane
(2-31) 1-Lithio-bis(3,7-tetrahydropyranyloxy)-octane

Alkoxyalkenyllithiums (2-32) 1-Lithio-3-tetrahydropyranyloxy-oct-trans-1-ene
(2-33) 1-Lithio-bis(3,7-tetrahydropyranyloxy)-oct-trans-1-ene
(2-34) 1-Lithio-3-tetrahydropyranyloxy-oct-trans-1-cis-5-diene

Alkoxyalkynyllithiums (2-35) 1-Lithio-3-(α-ethoxy-ethoxy-oct-5-yne

Siloxyalkenyllithiums (2-36) 1-Lithio-3-t-butyldimethylsiloxy-oct-trans-1-ene.

The cuprous salts that can be reacted with the organic lithium compounds to form the organic copper lithium compounds (II) may, for example, by cuprous chloride, cuprous bromide, cuprous iodide, and cuprous cyanide.

One specific example of preparing the organic copper lithium compound from the organic lithium compound and the cuprous salt comprises reacting the organic lithium compound with the cuprous salt at room temperature to −78° C. for several hours, for example, at −78° C. for 0.5 hour, using an inert medium such as a hydrocarbon (e.g., pentane, hexane or heptane) or an ether (e.g., diethyl ether, tetrahydrofuran, dioxane, or dimethoxyethane).

The compound of the formula [II] may be used as a complex with a trivalent phosphorus compound such as trialkylphosphines (e.g., triethylphosphine or tri-n-butylphosphine), trialkyl phosphites (e.g., trimethyl phosphite, triisopropyl phosphite, or tri-n-butyl phosphite) or triphenylphosphine. Frequently, the use of the complex tends to give an increased yield of the final product.

According to the process of this invention, the α,β-unsaturated carbonyl compound is first reacted with the above organic copper lithium compound in the presence of an aprotic organic medium.

The α,β-unsaturated carbonyl compound and the organic copper lithium compound are reacted stoichiometrically. Usually, the α,β-unsaturated carbonyl compound is used in a proportion of 0.5 to 2 mols, preferably 0.8 to 1.2 mols, per mol of the organic copper lithium compound.

The reaction temperature is −78° C. to about 50° C. It is sufficient, however, that the reaction is performed at room temperature for 10 minutes to 2 hours. The reaction proceeds sufficiently even when the temperature is lower than the above-specified range, for example, when it is −100° C.

The reaction is carried out in the presence of an aprotic organic medium which is liquid at the reaction temperature and not reactive with the reaction reagents. Such aprotic inert organic media includes a variety of aprotic inert liquid media including nitrogen-containing, sulfur-containing or oxygen-containing aprotic polar organic solvents. Examples of these organic media are saturated hydrocarbons such as pentane, hexane, heptane or cyclohexane, aromatic hydrocarbons such as benzene, toluene or oxylene, ethers such as diethyl ether, tetrahydrofuran, dioxane, dimethoxyethane, or diethylene glycol dimethyl ether, hexamethylphosphoric triamide, N,N-dimethylformamide, N,N-dimethylacetamide, dimethyl sulfoxide, sulfolane and N-methylpyrrolidone. Inert solvents such as pentane which are used to produce the organic copper lithium compounds can be used directly as such aprotic organic solvents. In this case, the starting α,β-unsaturated carbonyl compound (I) is added to the reaction system in which the organic copper lithium compound has been prepared.

SECOND STEP

II-1. Reaction agent in the second step

According to the process of this invention, the reaction product obtained by the reaction in the first step is reacted with an acid anhydride or an acid halide derived from an organic carboxylic acid having the following formula $$R_A\text{—COOH} \qquad \text{(III)}$$

wherein $R_A$ is a monovalent organic group, in the presence of an aprotic inert organic solvent, preferably in the co-presence of a nitrogen-containing, sulfur-containing or oxygen-containing aprotic organic solvent to form the desired 1,3-dicarbonyl compound of formula (IV) (second step).

Suitable $R_A$ groups are those containing 1 to 20 carbon atoms.

The acid halides are especially suitable as the reaction agent in the second step.

Suitable acid halides or acid anhydrides derived from the organic carboxylic acids of formula (III) are acid halides of the following formula $$R'_A\text{—COX} \qquad \text{(III-A)}$$

wherein $R'_A$ is a monovalent organic group containing 1 to 20 carbon atoms, and X is a halogen atom, or acid anhydrides of the following formulae

(III-B)

(III-C)

wherein $R'_A$ is a monovalent organic group containing 1 to 20 carbon atoms, and $R''_A$ is a divalent organic group containing 2 to 20 carbon atoms.

The acid halides of formula (III-A) are especially preferred. Of the acid halides, acid chlorides are preferred because they have sufficient reactivity and are readily available.

Of these, acid halides or acid anhydrides of the following formulae

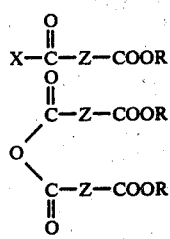

(III-A')

(III-B')

wherein Z is a divalent saturated or unsaturated hydrocarbon residue containing 1 to 19 carbon atoms; R is a hydrogen atom or a saturated or unsaturated hydrocarbon residue containing 1 to 8 carbon atoms; and X is a halogen atom,
are preferred. The acid halides of formula (III-A') are especially preferred.

Specific examples of these acid halides and acid anhydrides are shown below.

II-1-A. Acid Halides

Acetyl chloride,
acetyl bromide,
acetyl iodide,
acetyl fluoride,
propionyl chloride,
propionyl bromide,
n-butyryl chloride,
isobutyryl chloride,
n-valeryl chloride,
isovaleryl chloride,
n-caproyl chloride,
enanthoyl chloride,
capryloyl chloride,
pelargonoyl chloride,
caprinoyl chloride,
undecanoyl chloride,
lauroyl chloride,
tridecanoyl chloride,
myristoyl chloride,
pentadecanoyl chloride,
palmitoyl chloride,
margaroyl chloride,
stearoyl chloride,
cyclopropanecarboxylic acid chloride,
cyclopentanecarboxylic acid chloride,
cyclohexanecarboxylic acid chloride,
trimethylacetyl chloride,
diethylacetyl chloride,
t-butylacetyl chloride,
acryloyl chloride,
crotonyl chloride,
methacryloyl chloride,
4-methyl-2-pentenoic acid chloride,
10-undecenoyl chloride,
oleyl chloride,
benzoyl chloride,
benzoyl bromide,
phenylacetyl chloride,
p-methylbenzoyl chloride,
β-phenylpropionyl chloride,
cinnamoyl chloride,
p-bromobenzoyl chloride,
o-chlorobenzoyl chloride,
methoxyacetyl chloride,
p-methoxybenzoyl chloride, p-acetylbenzoyl chloride,
2-furoyl chloride,
α-thienoyl chloride,
2-thienylacetyl chloride,
nicotinoyl chloride,
methoxalyl chloride,
ethoxyalyl chloride,
β-carbomethoxypropionyl chloride,
γ-carboethoxybutyryl chloride,
γ-carboethoxyvaleroyl chloride,
ω-carboethoxycaproyl chloride,
ω-carboethoxyvaleroyl chloride,
ω-carboethoxyenanthoyl chloride,
ω-carboethoxycaprylyl chloride,
o-carbomethoxybenzoyl chloride,
m-carbomethoxybenzoyl chloride,
p-carbomethoxybenzoyl chloride,
cyanoacetyl chloride,
oxalyl chloride,
oxalyl bromide,
succinoyl chloride,
adipoyl chloride,
1,4-cyclohexanedicarboxylic acid chloride,
phthaloyl chloride,
isophthaloyl chloride, and
terephthaloyl chloride.

II-1-B. Acid Anhydrides

Acetic anhydride,
propionic anhydride,
n-butyric anhydride,
n-valeric anhydride,
n-caproic anhydride,
enanthoic anhydride,
n-caprylic anhydride,
pelargonic anhydride,
n-capric anhydride,
undecanoic anhydride,
lauric anhydride,
tridecanoic anhydride,
myristic anhydride,
pentadecanoic anhydride,
palmitic anhydride,
margaric anhydride,
stearic anhydride,
isobutyric anhydride,
isovaleric anhydride,
cyclobutanecarboxylic anhydride,
cyclohexanecarboxylic anhydride,
crotonic anhydride,
oleic anhydride,
vaccenic anhydride,
linoleic anhydride,
linolenic anhydride,
benzoic anhydride,
phenylacetic anhydride,
o-toluic anhydride,
m-toluic anhydride,
p-toluic anhydride,
p-methoxybenzoic anhydride,
p-bromobenzoic anhydride,
p-chlorobenzoic anhydride,
α-naphthenic anhydride,
diphenylacetic anhydride, succinic anhydride,
glutaric anhydride,
cis-1,2-cyclobutanedicarboxylic anhydride,
1,2-cyclohexanedicarboxylic anhydride,
5-norbornene-2,3-dicarboxylic anhydride,
maleic anhydride, and
phthalic anhydride.

The acid halides and acid anhydrides that can be used in this invention are, of course, not limited to the above-illustrated species.

II-2. Reaction Conditions in the Second Step (C-Acylation)

The reaction of the reaction product of the first step with the above acid halide or anhydride is carried out in an aprotic inert solvent. Alternatively, it can be carried out advantageously in an aprotic inert solvent in the co-presence of a Lewis acid and/or an aprotic polar organic compound, and this method often brings about an appreciable increase in yield.

Examples of the aprotic inert solvent are hydrocarbons such as pentane, hexane, heptane, cyclohexane, benzene, toluene, or xylene, which have already been described with regard to the first step, and also ethers such as diethyl ether, tetrahydrofuran, dioxane, dimethoxyethane, triethylene glycol dimethyl ether, or diethylene glycol dimethyl ether. Examples of the Lewis acid are aluminum fluoride, aluminum chloride, aluminum bromide, aluminum iodide, boron trifluoride, boron trichloride, boron tribromide, zinc chloride, zinc bromide, stannic chloride, stannic bromide, ferric chloride, titanium tetrachloride, or antimony trifluoride.

Examples of the aprotic polar compound used together with the aprotic inert solvent in performing the second-step reaction of this invention include hexamethylphosphoric triamide, N,N-dimethylformamide, dimethyl sulfoxide, formaldehyde dimethyl mercaptal S-oxide, sulfolane, N-methylpyrrolidone, tetramethylurea, acetonitrile, nitrobenzene, dimethylcyanamide, tetramethylethylenediamine, tetraethylethylenediamine, triethylenediamine, triethylamine, pyridine, α,α'-dipyridyl, 1,5-diazabicyclo[4,3-0]-5-nonene, and 1,5-diazabicyclo[5,4,0]-5-undecene.

The reaction can be preferably carried out by bringing the reaction product of the first step into intimate contact with the acid halide or anhydride in the presence of the above solvent at a temperature of −78° C. to about 50° C.

Preferably, the above solvent is used in a total amount of about 0.8 to about 100 mol times, preferably about 10 to 50 mol times, the amount of the α,β-unsaturated carbonyl compound as a starting material in the first step. The amount of the solvent, however, is not limited to this preferred range.

The acid anhydride or acid halide as a reaction agent can be used in an amount of about 0.5 to about 10 mol times, preferably 0.8 to 5 mol times, the amount of the starting α,β-unsaturated carbonyl compound. The amount of the Lewis acid optionally used in not more than 5 molar times the amount of the acid anhydride or acid halide.

The reaction proceeds sufficiently at a temperature of not more than 50° C., preferably 0° to 40° C., more preferably 10° to 30° C., for 0.5 to about 30 hours.

The 1,3-dicarbonyl compound of formula (IV) is separated and purified in the following manner after the reaction.

The reaction product is treated with water or an aqueous solution of a strong electrolyte for about 0.1 to 1 hour to hydrolyze it, and neutralized if desired. The product so treated is then extracted with ether such as diethyl ether, a saturated hydrocarbon such as pentane or hexane, an aromatic hydrocarbon such as benzene or toluene, or a halogenated hydrocarbon such as methylene chloride or chloroform. The organic phase extracted is sufficiently washed with water or an aqueous solution of a strong electrolyte, or if desired, with a dilute acid, thoroughly dried with anhydrous sodium sulfate, and concentrated to obtain a crude product. The crude product is purified by distillation or column chromatography to afford highly pure 1,3-dicarbonyl compounds of formula (IV).

The process of this invention described above can thus give 1,3-dicarbonyl compounds of formula (IV).

Of the 1,3-dicarbonyl compounds prepared by the present invention, 2-acyl-3-substituted cyclopentan-1-ones of the following formula

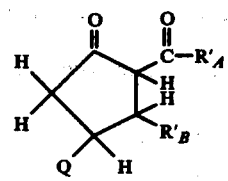

(IV-A)

wherein Q is a hydrogen atom, a hydroxyl group, or a protected hydroxyl group; $R'_A$ is a monovalent organic group containing 1 to 20 carbon atoms; and $R'_B$ is a monovalent organic group containing 2 to 20 carbon atoms,
especially those of the following formula

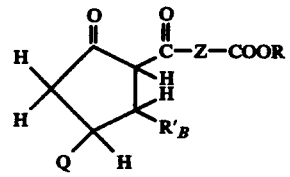

(IV-B)

wherein Q and $R'_B$ are the same as defined in formula (IV-A) above; Z is a divalent saturated or unsaturated hydrocarbon residue containing 1 to 19 carbon atoms; and R is a hydrogen atom or a saturated or unsaturated hydrocarbon residue containing 1 to 8 carbon atoms, and 2-acyl-3-substituted cyclohexan-1-ones of the following formula

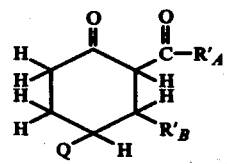

(IV-C)

wherein Q is a hydrogen atom, a hydroxyl group, or a protected hydroxyl group; $R'_A$ is a monovalent organic group containing 1 to 20 carbon atoms; and $R'_B$ is a monovalent organic group containing 2 to 20 carbon atoms,
especially those of the following formula

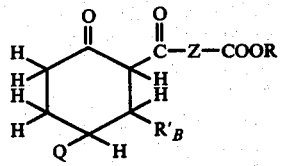

wherein Q and $R'_B$ are the same as defined in formula (IV-C); Z is a divalent saturated or unsaturated hydrocarbon residue containing 1 to 19 carbon atoms; and R is a hydrogen atom or a saturated or unsaturated hydrocarbon residue containing 1 to 8 carbon atoms, are novel compounds, and are useful for preparing medicines, agricultural chemicals, perfumes, etc.

Furthermore, 2-acyl-3-substituted cyclopentan-1-ones of the following formula

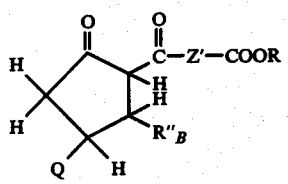

Q is a hydrogen atom, a hydroxyl group or a protected hydroxyl group; $Z'$ is a divalent saturated or unsaturated hydrocarbon residue containing 5 to 10 carbon atoms; and $R''_B$ is a saturated or unsaturated hydrocarbon residue containing 8 to 20 carbon atoms, which may contain 1 to 3 hydroxyl groups or protected hydroxyl groups, are novel compounds and oxo analogs of prostaglandin $E_1$ having various important physiological effects such as smooth muscle shrinking activity, hypotensive activity, bronchodilating activity, or activity for inhibiting liberation of fatty acids.

The following Examples illustrate the present invention in greater detail.

EXAMPLE 1

(a) Preparation of Organic Copper Lithium Compound

To 2 ml of anhydrous diethyl ether was added 136 mg (2 mmol) of 1-pentyne, and 1.5 ml (2 mmol) of a 1.3 M ether solution of methyllithium was added dropwise at 0° C. in an atmosphere of nitrogen. The mixture was then stirred for 15 minutes, and the resulting solution was added to 1 ml. of anhydrous diethyl ether containing 380 mg (2 mmol) of cuprous iodide, and the mixture was stirred at 0° C. for 15 minutes to afford an anhydrous diethyl ether solution of copper pentylide.

On the other hand, 736 mg (2 mmol) of 3-t-butyldimethylsiloxy-1-iodo-trans-1-octene was added to 2 ml. of anhydrous hexane, and 1.4 ml. (2 mmol) of a 1.4 M hexane solution of n-butyllithium was added. The mixture was stirred at −78° C. for 30 minutes in an atmosphere of nitrogen to afford an anhydrous hexane solution of 3-t-butyldimethylsiloxy-1-lithio-trans-1-octene. The resulting solution was added dropwise to the anhydrous diethyl ether solution of copper pentylide obtained previously, and the mixture was stirred at −78° C. for 30 minutes to afford a solution of an organic copper lithium compound of the following formula

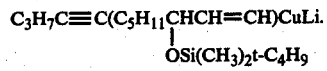

(b) β-Alkylation and α-Acylation

A solution of 164 mg (2 mmol) of cyclopent-2-en-1-one in 1 ml. of diethyl ether was added to the solution of the organic copper lithium compound prepared in (a) above, and the mixture was stirred at −78° C. for 30 minutes (β-alkylation). Then, a solution of 1.24 g (6 mmol) of ω-carboethoxycaproyl chloride in a mixture of 3 ml. of of diethyl ether and 10 ml. of tetrahydrofuran, and the mixture was stirred at room temperature for 3 hours (α-acylation).

(c) Separation and Purification of the Reaction Product

The tetrahydrofuran was removed at reduced pressure from the reaction mixture obtained in (b) above, and an aqueous solution of ammonium chloride containing a small amount of ammonia was added. The mixture was stirred, and extracted with petroleum ether. The petroleum ether phase was washed thoroughly with water, and then with an aqueous solution of sodium chloride, dried with anhydrous sodium sulfate, and concentrated to afford 1.42 g of a crude reaction product. The crude product was subjected to column chromatography (carrier, silica gel; developing solvent, a 1:2 (volume) mixture of diethyl ether and petroleum ether), and again purified by preparative thin-layer chromatography to afford a purified product (liquid) in an amount of 100 mg.

(d) Identification of the Reaction Product

The purified product gave the following spectral data.

Infrared (liquid film), characteristic absorptions ($cm^{-1}$) at: 1730, 1720, 1630, 1170, 1030, 830, and 770.

Nuclear magnetic resonance absorption [carbon tetrachloride, δ (ppm)]: 0.08 (6H; silyl methyl group); 0.93 (12H; t-butyl group, and methyl group of side chain); 1.29 (3H; methyl group of ethyl ester); 1.3–1.8 (16H; methylene group); 2.1–2.6 (7H; methylene and methine groups adjacent to carbonyl or olefin group); about 3.6 (2H; methine group to which siloxy group is attached, and methine group of β-diketone); 4.16 (2H; methylene group of ethyl ester); 5.4–5.7 (2H; olefin proton).

Mass analysis (70 eV, m/e): 494 ($M^+$), 479 (M—$CH_3$), 449 (M—$OC_2H_5$), 437 (M—$C_4H_9$).

Thin-layer chromatography (developing solvent; ether/n-hexane): $R_f$ = 0.43.

Gas chromatography (Stationary phase, JXR-silicone 10%, 1 m, the temperature elevated from 150 to 260° C. at a rate of 10° C./min): Retention time: 20 minutes 17 seconds.

From the above data, the resulting product was identified as an ethyl ester of 15-t-butyldimethylsiloxy-7-oxo-11-deoxyprostaglandin $E_1$.

It was ascertained from the gas chromatographic analysis of the crude reaction product that the yield of this product was about 26%.

The ethyl ester so obtained was dissolved in a mixture consisting of 2 ml of acetic acid, 1 ml of water and 1 ml of tetrahydrofuran, and the mixture stirred at room temperature for 20 hours. Then, it was concentrated to afford about 80 mg of a crude product. The crude product was subjected to preparative thin-layer chromatography (developing solvent: diethyl ether), and a fraction having an $R_f$ of 0.38 was separated to afford 10 mg of a liquid purified product. This product gave the following spectral data.

Infrared absorption (liquid film), characteristic absorptions at (cm$^{-1}$): 3450, 1730, 1710, 1635, 1170, 1030, and 975.

Nuclear magnetic resonance absorption (deuterochloroform, δ (ppm)): 0.89 (3H; methyl group of side chain); 1.2-1.8 (16H; methylene group); 2.1-2.7 (7H; methylene and methine groups adjacent to carbonyl or olefin group); 1.24 (3H; methyl group of ethyl ester); 4.13 (2H; methylene group of ethyl ester); 3.5-4.2 (3H; methine group to which alcohol is bonded, proton of alcohol, or methine group of β-diketone); 3.5-4.2 (2H; olefin proton).

Mass analysis (m/e): 362 (M—H$_2$O, 70 eV), 380 (M$^+$, 70 eV and 11eV, a direct inlet method).

Thin-layer chromatography (developing solvent; ether): $R_f = 0.38$.

From the above data, this product was identified as an ethyl ester of 7-oxo-11-deoxyprostaglandin E$_1$.

EXAMPLE 2

(a) Preparation of Organic Copper Lithium Compound

To 2 ml of anhydrous diethyl ether were added 82 mg (1.2 mmol) of 1-pentyne, and 0.95 ml (1.2 mmol) of a 1.3 M ether solution of methyllithium. The mixture was stirred at 0° C. for 15 minutes in an atmosphere of nitrogen. The solution was added to 1 ml of anhydrous diethyl ether containing 230 mg (1.2 mmol) of cuprous iodide, and the mixture was stirred at 0° C. for 15 minutes in an atmosphere of nitrogen to afford an anhydrous diethyl ether solution of copper pentylide.

On the other hand, 442 mg (1.2 mmol) of 3-t-butyldimethylsiloxy-1-iodo-trans-1-octene was added to 2 ml of anhydrous hexane, and 1 ml (1.2 mmol) of a 1.2 M hexane solution of n-butyllithium was added. The mixture was stirred at −78° C. for 30 minutes in an atmosphere of nitrogen to afford an anhydrous hexane solution of 3-t-butyldimethylsiloxy-1-lithio-trans-1-octene. The resulting solution was added dropwise to the anhydrous diethyl ether solution of copper pentylide prepared previously, and the mixture was stirred at −78° C. for 30 minutes in an atmosphere of nitrogen to afford a solution of an organic copper lithium compound of the following formula

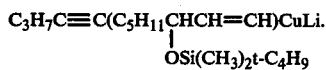

(b) β-Alkylation and α-Acylation

A solution of 212 mg (1 mmol) of 4-t-butyldimethylsiloxycyclopent-2-en-1-one in 1 ml of diethyl ether was added to the solution of the organic copper lithium compound prepared in (a) above, and the mixture stirred at −78° C. for 30 minutes (β-alkylation). During this time, the reaction solution turned from yellow to light yellow via orange. Then, to the resulting solution was added a solution of 1.03 g (5 mmol) of ω-carboethoxycaproyl chloride in a mixture consisting of 5 ml of tetrahydrofuran and 2 ml of hexamethylphosphoric triamide (HMPA), and the mixture was stirred at room temperature for 1 hour (α-acylation). The reaction solution turned brown.

(c) Separation and Purification of the Reaction Product

The tetrahydrofuran was removed at reduced pressure from the reaction mixture obtained in (b) above, and then an aqueous solution of ammonium chloride was added. The mixture was then neutralized with sodium bicarbonate (whereby the pH changed from 1 to 6), and extracted with petroleum ether. The petroleum ether phase was washed thoroughly with water and then with an aqueous solution of sodium chloride, dried with anhydrous sodium sulfate, and concentrated to afford 1.29 g of a crude reaction product. The crude product was subjected to column chromatography (carrier, silica gel; developing solvent, ethyl ether) to afford 970 mg of a purified reaction product (liquid). The product was further purified by preparative thin-layer chromatography, and identified.

(d) Identification of the Reaction Product

The above purified product gave the following spectral data.

Infrared absorption (liquid film), characteristic absorptions at (cm$^{-1}$): 1730, 1635, 840, 775.

Mass analysis (70 eV, m/e): 624 (M$^+$, detected at 11 eV), 609 (M—CH$_3$), 579 (M—OC$_2$H$_5$), 567 (M—C$_4$H$_9$), 492 (M—HOSi (CH$_3$)$_2$ t—C$_4$H$_9$).

Thin-layer chromatography (developing solvent, diethyl ether): $R_f = 0.54$.

Gas chromatography (stationary phase, OV-1 15%, 2m, 280° C.): Retention time; 6 minutes 50 seconds Nuclear magnetic resonance absorption (carbon tetrachloride, δ (ppm)): 0.08 (12H; silylmethyl group); 0.93 (21H; t-butyl group, and methyl group of side chain); 1.29 (3H; methyl group of ethyl ester); 1.3-1.8 (14H; methylene group); 2.1-2.6 (7H; methylene and methine groups adjacent to carbonyl or olefin group); about 3.6 (3H; methyl group to which siloxy group is bonded, and methine group of β-diketone); 4.16 (2H; methylene group of ethyl ester); 5.4-5.7 (2H; olefin proton).

From the above data, this product was identified as an ethyl ester of 7-oxo-11,15-bis(t-butyldimethylsiloxy)-prostaglandin E$_1$.

830 mg of the above ethyl ester was dissolved in a mixture consisting of 60 ml of acetic acid and 20 ml of water. The mixture was stirred at room temperature for 18 hours, and concentrated to afford 691 mg of a crude product. The crude product was subjected to preparative thin-layer chromatography (developing solvent, diethyl ether), and 156 mg of a fraction was collected. This fraction was further subjected to preparative thin-layer chromatography (developing solvent, diethyl ether) to afford 35 mg of a purified product (in a yield of 16% based on the crude product).

This pure product gave the following spectral data.

Infrared absorption (liquid film), characteristic absorptions (cm$^{-1}$) at: 3400, 1730, 1715, 1635, 1180, 1030, 975.

Nuclear magnetic resonance absorption (deuterochloroform, δ (ppm)): 0.90 (3H; methyl group of side chain); 1.24 (3H; methyl group of ethyl ester); 1.2-1.8 (14H; methylene group); 2.1-2.7 (7H; methylene and methine groups adjacent to carbonyl or olefin group); about 2.6 (2H; alcohol proton); 2.8-3.7 (3H; methine group bonded to alcohol, and methine group of β-diketone); 4.07 (2H; methylene group of ethyl ester); 5.4-5.7 (2H; olefin proton).

Mass analysis (direct inlet method, 11eV, m/e): 396 (M+, slightly appreciable), 378 (M—H$_2$O), 368 (M—28), 360 (M—H$_2$O × 2).

Thin-layer chromatography: R$_f$ = 0.08 (ethyl ether) R$_f$ = 0.34 (ethyl acetate)

From the above data, this product was identified as an ethyl ester of 7-oxoprostaglandin E$_1$.

EXAMPLE 3

To 25 ml of anhydrous diethyl ether was added 950 mg (5 mmol) of cuprous iodide, and the mixture was cooled to −78° C. in an atmosphere of nitrogen. To the solution was added 17 ml (10 mmol) of a 0.58 M ether solution of ethyllithium, and the mixture stirred for 30 minutes (the preparation of lithium diethylcuprate). Then, a solution of 480 mg (5 mmol) of cyclohex-2-en-1-one in 1 ml of ether was added dropwise, and the mixture was stirred at −78° C. for 30 minutes (β-alkylation). A mixture consisting of 2.2 g (28 mmol) of acetyl chloride, 2 ml of hexamethyl phosphoric triamide (HMPA) and 10 ml of tetrahydrofuran was added to the mixture. The mixture was continuously stirred for one hour while raising the temperature gradually to room temperature (α-acetylation). The resulting reaction mixture was evaporated at reduced pressure by means of a rotary evaporator to remove the tetrahydrofuran from it. An aqueous solution of sodium bicarbonate was added to the concentrated mixture to hydrolyze and neutralize it. The mixture was then extracted with ether. The ethereal phase was washed thoroughly with water, dried with anhydrous sodium sulfate, and concentrated to afford 1.26 g of a crude product. When this crude product was analyzed by thin-layer chromatography, a spot capable of being colored brown with a methanol solution of ferric chloride was seen at an R$_f$ of 0.65 (developing solvent, diethyl ether). A fraction corresponding to this spot was separated by preparative thin-layer chromatography (developing solvent, diethyl ether) to afford 605 mg of a liquid. This liquid product gave the following spectral data, and was identified as 2-acetyl-3-ethylcyclohexan-1-one. The amount of 605 mg corresponded to 3.6 mmol, and the yield was 72%.

Thin-layer chromatography (developing solvent, diethyl ether): R$_f$ = 0.65.

Infrared absorption (liquid film, cm$^{-1}$): 3400, 1720, 1690, 1600

Nuclear magnetic resonance absorption (CCl$_4$, δ (ppm)): 0.93 (3H; methyl group); 2.07 (3H; methyl group of acetyl group); 1.3-2.5 (9H; methylene group); 16.10 (1H, methine group between ketone groups).

Mass analysis (70 eV, m/e): 168 (molecular ion).

EXAMPLE 4

To 20 ml of anhydrous diethyl ether were added 1.9 g (10 mmol) of cuprous iodide and 2.0 g (10 mmol of tri-n-butylphosphine, and the mixture was stirred at room temperature for about 30 minutes in an atmosphere of nitrogen. The mixture was then cooled to −78° C., and 12.8 mg (20 mmol) of a 15% by weight hexane solution of n-butyllithium was added, followed by stirring for 30 minutes. Then, a solution of 700 mg (10 mmol) of methyl vinyl ketone in 10 ml of ether was added, and the mixture stirred at −78° C. for 1 hour. Then, 5 ml of hexamethylphosphoric triamide was added, and the mixture was stirred at room temperature for about 10 minutes. Furthermore, a solution of 3.53 g (25 mmol) of benzoyl chloride in 20 ml of ether was added, and the mixture was stirred at room temperature for one hour. After the reaction, 50 ml of a saturated ammoniac aqueous solution of ammonium chloride was added, and the mixture stirred at room temperature for about 30 minutes. The mixture was post-treated (pH 4), extracted with ether, washed, and dried with anhydrous sodium sulfate. The dried product was concentrated to afford 12.326 g of a crude product. The crude product was purified by column chromatography (silica gel).

There was obtained 1.198 g (5.2 mmol) of 3-benzoyl-2-octanone in a yield of 52%. This product gave the following spectral data.

Infrared absorption (liquid film, cm$^{-1}$): 3050, 1720, 1680, 1600, 1580, 710, 690

Nuclear magnetic resonance absorption (carbon tetrachloride, δ (ppm)): 0.90 (3H; methyl group); 1.1-1.9 (8H; methylene group); 2.02 (3H; methyl group of methyl ketone); 7.2-7.5 (3H; proton of benzene ring); 7.7-8.1 (2H; proton of benzene ring).

Mass analysis (m/e): 232 (molecular ion)

EXAMPLE 5

To 10 ml of anhydrous diethyl ether was added 380 mg (2 mmol) of cuprous iodide, and the mixture was cooled to −78° C. in an atmosphere of nitrogen. Then, 3 ml (4 mmol) of a 1.33 M hexane solution of n-butyllithium was added to the resulting solution, and the mixture stirred for 30 minutes. A solution of 252 mg (2 mmol) of n-amyl vinyl ketone in 0.5 ml of ether was added, and the mixture stirred at −78° C. for one hour. Furthermore, a mixture consisting of 800 mg (6 mmol) of n-caproyl chloride, 0.5 ml of hexamethylphosphoric triamide and 3 ml of ether was added to the mixture, and the mixture was continuously stirred for 2 hours while raising the temperature gradually to room temperature. Then, an aqueous solution of sodium bicarbonate was added to the mixture to hydrolyze and neutralize it. The neutralized mixture was extracted with ether. The resulting ethereal phase was thoroughly washed with water, dried with anhydrous sodium sulfate, and concentrated to afford 510 mg of a crude product. The crude product was subjected to preparative thin-layer chromatography (developing solvent, a 1:2 mixture of n-hexane and ether), to afford 250 mg of a liquid capable of being colored by addition of ferric chloride. This liquid product gave the following spectral data, and was identified as 7-n-pentyltridecane-6,8-dione. The amount of 250 mg corresponded to 0.89 mmol, and the yield was 44%.

Infrared absorption (liquid film, cm$^{-1}$): 3350, 1720, 1690, 1600

Nuclear magnetic resonance absorption (CCl$_4$, δ (ppm)): 0.87 (9H, CH$_3$); 1.20 (20H; —CH$_2$—); 2.40 (4H, —CH$_2$— adjacent to C=O); 16.10 (1H; CH between two ketone groups).

Mass analysis (70 eV, m/e): 282 molecular ion)

EXAMPLE 6

In the same way as in Example 4, 12.9 ml (20 mmol) of a 15% by weight hexane solution of n-butyllithium was reacted for one hour with a solution of 960 mg (10 mmol) of 2-cyclohexenone in 10 ml of ether in the presence of 1.9 g (10 mmol) of cuprous iodide and 2.0 g (10 mmol) of tri-n-butylphosphine. Then, 5 ml of hexamethylphosphoric triamide was added, and the mixture was stirred for about 10 minutes. Further, a solution of 3.93 g (50 mmol) of acetyl chloride in 20 ml of ether was added gradually to the mixture at −78° C., and after the addition, the mixture was stirred continuously for 1 hour at room temperature. After the reaction, the reaction product was post-treated, extracted, washed, and dried in the same way as in Example 4 to afford 6.384 g of a crude product. The crude product was purified by distillation at reduced pressure. There were obtained 40 mg (0.3 mmol) of 3-n-butylcyclohexanone as a by-product in a yield of 3%, and 1.578 g (8.1 mmol) of 2-acetyl-3-n-butylcyclohexanone as a main product in a yield of 81%. The product gave the following spectral data.

Infrared absorption (liquid film, cm$^{-1}$): 1720, 1700, 1600.

Nuclear magnetic resonance absorption (carbon tetrachloride, δ (ppm)): 0.90 (3H; —CH$_3$); 2.10 (3H; —CH$_3$ of CH$_3$CO—); 1.1–2.4 (13H; —CH$_2$—); 16.13 (1H; CH between two ketone groups).

Mass analysis (70 eV, m/e): 196 (molecular ion)

EXAMPLE 7

In the same way as in Example 4, 15.3 ml (20 mmol) of a 1.31 M hexane solution of n-butyllithium was reacged with a solution of 960 mg (10 mmol) of 2-cyclohexenone in 5 ml of ether at −78° C. for 30 minutes in the presence of 3.90 g (10 mmol) of tri-n-butylphosphine-copper (I) iodide complex. Then, a mixture consisting of 4 ml (56 mmol) of acetyl chloride, 5 ml of hexamethylphosphoric triamide and 10 ml of ether was rapidly added, and the mixture was stirred for 4 hours while gradually raising the temperature to room temperature. After the reaction, the reaction product was post-treated, extracted, washed, and dried in the same way as in Example 4 to afford 5.48 g of a crude product. The crude product was purified by distillation at reduced pressure to afford 1.81 g of 2-acetyl-3-n-butylcyclohexanone (boiling point 64°–66° C./0.06 mmHg, 92%).

EXAMPLE 8

To 20 ml of anhydrous diethyl ether was added 1.9 g (10 mmol) of cuprous iodide, and at −78° C. in an atmosphere of nitrogen, 12.8 ml (20 mmol) of a 15% by weight hexane solution of n-butyllithium was added. The mixture was stirred for 30 minutes, and then, 960 mg (10 mmol) of 2-cyclohexenone was added. The mixture was further stirred for one hour. Then, 3.93 g (50 mmol) of acetyl chloride was added, and the mixture was stirred for 2 hours at room temperature. After the reaction, the reaction product was post-treated, extracted, washed, and dried in the same way as in Example 4 to afford 2.662 g of a crude product. The crude product was purified by column chromatography (silica gel) to afford 56 mg (0.4 mmol) of 3-n-butylcyclohexanone as a by-product in a yield of 4% and 1.103 g (5.6 mmol) of 2-acetyl-3-n-butylcyclohexanone as a main product in a yield of 56%.

EXAMPLE 9

In the same way as in Example 4, 12.8 ml (20 mmol) of a 15% by weight hexane solution of n-butyllithium was reacted with 960 mg (10 mmol) of a solution of 960 mg (10 mmol) of 2-cyclohexenone in 10 ml of ether for one hour in the presence of 1.9 g (10 mmol) of cuprous iodide and 2.0 g (10 mmol) of tri-n-butylphosphone. Then, 5 ml of hexamethylphosphoric triamide was added, and the mixture stirred for about 10 minutes. Furthermore, a solution of 5.1 g (50 mmol) of acetic anhydride in 20 ml of ether was added, and the mixture was stirred for an additional 2.5 hours at room temperature. After the reaction, the reaction product was post-treated, extracted, washed, and dried in the same way as in Example 4 to afford 2.285 g of a crude product. The crude product was purified by column chromatography to afford 81 mg (0.5 mmol) of 3-n-butylcyclohexanone as a by-product in a yield of 5%, and 98 mg (0.5 mmol) of 2-acetyl-3-n-butylcyclohexanone as a product in a yield of 5%.

EXAMPLE 10

In the same way as in Example 4, 12.8 ml (20 mmol) of a 15% by weight hexane solution of n-butyllithium was reacted with a solution of 960 mg (10 mmol) of 2-cyclohexenone in 10 ml of ether at −78° C. for 1 hour with stirring in the presence of 1.9 g (10 mmol) of cuprous iodide and 2.0 g (10 mmol) of tri-n-butylphosphine. Then, 5 ml of hexamethylphosphoric triamide was added, and the mixture was further stirred for about 10 minutes. The resulting solution was added dropwise at 0° C. to a solution prepared by adding 2.66 g (20 mmol) of aluminum chloride and 2.04 g (20 mmol) of acetic anhydride to 20 ml of anhydrous diethyl ether, and stirring the mixture for about 30 minutes at 0° C. in an atmosphere of nitrogen. The mixture was stirred for an additional 2 hours at room temperature, and then, post-treated, extracted, washed and dried in the same way as in Example 4 to afford 9.251 g of a crude product. The crude product was distilled at reduced pressure to afford 564 mg (3.7 mmol) of 3-n-butylcyclohexanone as a by-product in a yield of 37% and 364 mg (1.9 mmol) of 2-acetyl-3-n-butylcyclohexanone as a product in a yield of 19%.

EXAMPLE 11

To 30 ml of anhydrous diethyl ether were added 1.5 g (10 mmol) of cuprous bromide and 2.5 g (20 mmol) of trimethyl phosphite, and the mixture stirred for about 1 hour at room temperature in an atmosphere of nitrogen. The mixture was cooled to −78° C., and 12.8 ml (20 mmol) of a 15% by weight hexane solution of n-butyllithium was added, followed by further stirring the mixture for 30 minutes. Then, 960 mg (10 mmol) of 2-cyclohexenone was added and reacted for 1 hour. After the reaction, 5 ml of tetramethylenediamine was added, and the mixture was stirred for about 10 minutes. The resulting solution was added dropwise at 0° C. to a solution prepared by adding 2.84 g (20 mmol) of a boron trifluoride-diethyl ether complex and 2.04 g (20 mmol) of acetic anhydride to 20 ml of anhydrous diethyl ether, and stirring the mixture at 0° C. for about 30 minutes in an atmosphere of nitrogen. Then, the mixture was stirred for an additional 3 hours at room temperature, and then, post-treated, extracted, washed with dilute hydrochloric acid, and dried in the same way as in Example 4 to afford 5.432 g of a crude product. The crude product was purified by distillation at reduced pressure to afford 370 mg (2.4 mmol) of 3-n-butylcyclohexanone in a yield of 24% and 170 mg (0.9 mmol) of 2-acetyl-3-n-butylcyclohexanone in a yield of 9%.

EXAMPLE 12

To 30 ml of anhydrous diethyl ether were added 3.8 g (20 mmol) of cuprous iodide and 4.0 g (20 mmol) of tri-n-butylphosphine, and the mixture was stirred for about 1 hour at room temperature in an atmosphere of nitrogen and then cooled to −78° C. Then, 25.6 ml (40 mmol) of a 15% by weight hexane solution of n-butyllithium was added, and the mixture was stirred for 30 minutes, and 1.92 g (20 mmol) of 2-cyclohexenone was added. The mixture was further stirred for 1 hour at −78° C. Then, 5 ml of hexamethylphosphoric triamide was added, and the mixture was stirred for about 10 minutes. Phthalic anhydride (2.96 g, 20 mmol) was further added, and the mixture was stirred for 3 hours at room temperature. After the reaction, a solution of 4 g (100 mmol) of sodium hydroxide in 50 ml of water was added, and the mixture was stirred for about 1 hour. It was extracted with ether, washed, and dried to afford 6.22 g of a crude product. The crude product was distilled to afford 1.62 g (10.5 mmol) of 3-n-butylcyclohexanone in a yield of 53%.

On the other hand, the aqueous phase after the ether extraction was acidified with hydrochloric acid, extracted with ethyl acetate, washed, and dried to afford 7.645 g of a crude product. The crude product was purified by column chromatography (silica gel), and recrystallized from a mixture of ethyl acetate and chloroform to afford 700 mg (23 mmol) of o-(2-oxo-6-n-butylcyclohexyl) carbonylbenzoic acid in a yield of 12%. This product gave the following spectral data.

Infrared absorption (liquid film, $cm^{-1}$): around 3000, 1690

Nuclear magnetic resonance absorption (deuterochloroform, $\delta$ (ppm)): 0.90 (3H, —$CH_3$); 1.0–1.6, 2.1–2.6 (14H; —$CH_2$—); 7.4–7.7, 7.7–8.1 (4H; proton of benzene ring); around 10.2 (1H; proton of carboxylic acid); disappeared upon treatment with heavy water.

Mass analysis (70 e/V, m/e): 302 (molecular ion).

EXAMPLE 13

In the same way as in Example 4, 12.8 ml (20 mmol) of a 15% by weight hexane solution of n-butyllithium was reacted with a solution of 820 ml (10 mmol) of 2-cyclopentenone in 10 ml of ether for 1 hour in the presence of 1.9 g (10 mmol) of cuprous iodide and 2.0 g (10 mmol) of tri-n-butylphosphine. Then, 5 ml of hexamethylphosphoric triamide was added, and the mixture was stirred for about 10 minutes. A solution of 3.93 g (50 mmol) of acetyl chloride in 20 ml of ether was added gradually at −78° C., and then, the mixture stirred for 1 hour at room temperature. After the reaction, the product was post-treated, extracted, washed and dried in the same way as in Example 4 to afford 10.781 g of a crude product. The crude product was purified by distillation at reduced pressure to afford 459 mg (3.3 mmol) of 3-n-butylcyclopentanone in a yield of 33% and 698 mg (3.8 mmol) of 2-acetyl-3-butylcyclopentanone in a yield of 38%. The latter product gave the following spectral data.

Infrared absorption (liquid film, $cm^{-1}$): 1740, 1710, 1650

Nuclear magnetic resonance absorption (carbon tetrachloride, $\delta$ (ppm)): 0.93 (3H; —$CH_3$); 1.1–1.7 (11H; —$CH_2$—); 2.00 (3H; —$CH_3$ of $CH_3CO$—).

Mass analysis (70 eV, m/e): 182 (molecular ion)

COMPARATIVE EXAMPLE

To 10 ml of anhydrous diethyl ether was added 950 ml (5 mmol) of cuprous iodide, and at 0° C. in an atmosphere of nitrogen, 7.8 ml (10 mmol) of a 1.30 M ether solution of methyllithium was added, followed by stirring for 15 minutes. Then, a solution of 480 mg (5 mmol) of cyclohex-2-en-1-one in 1 ml of ether was added dropwise to the mixture, and the stirring was continued for 1 hour at 0° C. Then, a mixture consisting of 1.6 g (20 mmol) of acetyl chloride, 1 ml of hexamethylphosphoric triamide and 3 ml of ether was added, and the mixture was stirred for 2 hours while raising the temperature gradually to room temperature. An aqueous solution of sodium bicarbonate was added to neutralize the reaction mixture, and it was then extracted with ether. The resulting ethereal phase was thoroughly washed with water. dried with anhydrous sodium sulfate, and concentrated to afford 800 mg of a crude product. The crude product was subjected to preparative thin-layer chromatography to afford 670 mg of a liquid. This liquid product corresponded in gas chromatogram, infrared absorption spectrum, nuclear magnetic resonance spectrum and mass spectrum with 1-acetoxy-3-methylcyclohex-1-ene prepared by reacting 3-methyl-cyclohexan-1-one with acetic anhydride in the presence of perchloric acid, and was thus identified as 1-acetoxy-3-methylcyclohex-1-ene.

The amount of 670 mg corresponded to 4.3 mmol and the yield was 86%.

Gas-chromatographic and various spectral analyses of the crude product showed that there was no appreciable formation of 2-acetyl-3-methylcyclohexanone.

What we claim is:

1. 2-Acyl-3-substituted cyclohexan-1-ones of the following formula

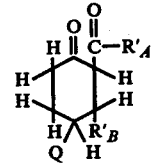

wherein Q is a hydrogen atom; $R'_A$ is a monovalent organic group of the formula:

Z—COOR wherein Z is a divalent saturated or unsaturated hydrocarbon residue containing 1 to 19 carbon atoms; and R is a hydrogen atom or a saturated or unsaturated hydrocarbon residue containing 1 to 8 carbon atoms; and $R'_B$ is an alkyl group containing 2 to 20 carbon atoms.

2. The 2-acyl-3-substituted cyclohexane-1-ones according to claim 1, which is o-(2-oxo-6-n-butylcyclohexyl) carbonyl benzoic acid.

* * * * *